United States Patent [19]

Lander

[11] Patent Number: 5,030,206

[45] Date of Patent: Jul. 9, 1991

[54] TROCAR

[75] Inventor: Jack R. Lander, Danbury, Conn.

[73] Assignee: United States Surgical Corporation, Norwalk, Conn.

[21] Appl. No.: 482,320

[22] Filed: Feb. 16, 1990

Related U.S. Application Data

[63] Continuation of Ser. No. 380,094, Jul. 14, 1989, Pat. No. 4,902,280, which is a continuation of Ser. No. 920,509, Oct. 17, 1986.

[51] Int. Cl.⁵ ............................................ A61M 5/178
[52] U.S. Cl. ..................................... 604/164; 606/185
[58] Field of Search ................. 604/51, 118, 164-170, 604/272-274; 606/185; 128/753, 754

[56]  References Cited

U.S. PATENT DOCUMENTS

| | | |
|---|---|---|
| 2,187,372 | 1/1940 | Capaldo . |
| 2,483,906 | 10/1949 | Lavarone . |
| 2,501,940 | 3/1950 | Hibbard . |
| 2,678,842 | 5/1954 | Usalis . |
| 2,950,134 | 8/1960 | Strange . |
| 3,468,568 | 9/1969 | Ulich . |
| 4,284,287 | 8/1981 | Esposito . |
| 4,418,707 | 12/1983 | Wu . |
| 4,601,710 | 7/1986 | Moll ..................... 604/165 |
| 4,654,030 | 3/1987 | Moll et al. ............. 604/272 |
| 4,738,663 | 4/1988 | Bogan ................... 604/198 |
| 4,911,693 | 3/1990 | Paris ..................... 604/198 |

FOREIGN PATENT DOCUMENTS 103373  5/1898  Fed. Rep. of Germany .

Primary Examiner—Stephen C. Pellegrino
Assistant Examiner—Michael Rafa
Attorney, Agent, or Firm—Thomas R. Bremer

[57]  ABSTRACT

The trocar is provided with a leaf spring in the housing which abuts a collar on a protective tube which surrounds the sharp tip of the stylet. A spring finger extending from the leaf spring is actuated by a slider when the two housings of the trocar components are squeezed together. The spring finger initially lifts the leaf spring from the collar to release the protective tube for sliding proximally while the collar subsequently lifts the spring finger from the shoulder of the slider to prevent a re-release of the leaf spring when the protective tube 16 is moved back into the extended position.

25 Claims, 3 Drawing Sheets

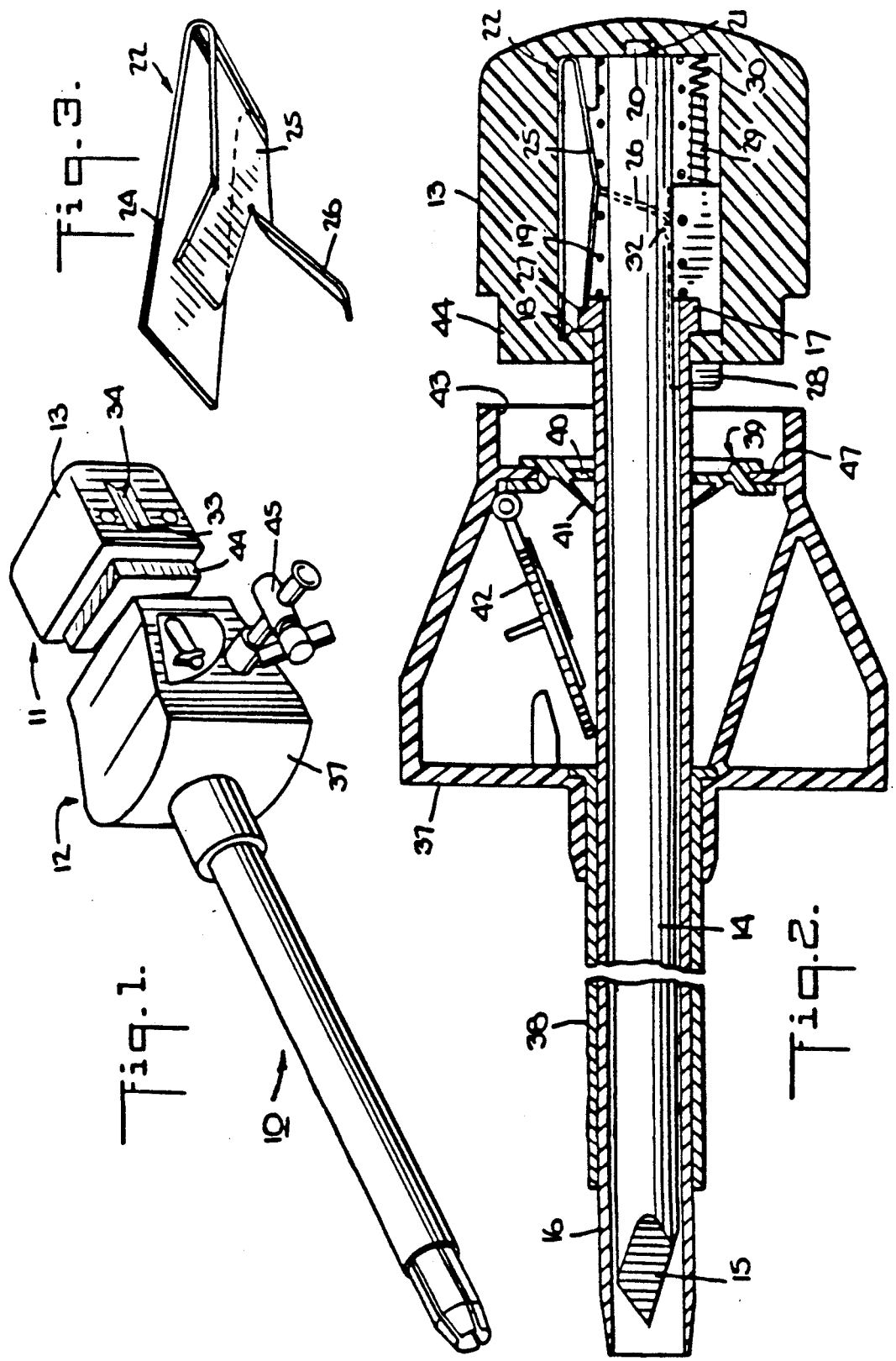

TROCAR

RELATED APPLICATIONS

This application is a continuation of co-pending application Ser. No. 07/380,094 filed July 14, 1989, now U.S. Pat. No. 4,902,280, 02/20/90 which is a continuation of co-pending application Ser. No. 06/920,509 filed Oct. 17, 1986.

TECHNICAL FIELD

This invention relates to a trocar. Particularly, this invention relates to a latch means for a trocar.

BACKGROUND AND OBJECTS OF THE INVENTION.

As is known, a trocar is generally made of a stylet having a sharp tip for penetrating through an abdominal wall and surrounding tube through which gas or the like may be injected or exhausted from the abdomen after puncturing by the stylet. Further, in order to protect a patient or surgeon from injury through inadvertent contact with the sharp tip, protective tubes have been positioned over the stylet tip, for example, as described in U.S. Pat. No. 4,601,710. In this case, the stylet is secured to a housing with a spring-biased protective tube concentrically about the stylet. When put to use, the protective tube is able to move proximally to expose the sharp tip for penetrating the abdominal wall without interference. Once a puncture has been made, the protective tube is able to slide distally under the force of the spring to again cover over the sharp tip to preclude injury to tissue within the abdomen. Thereafter, the stylet can be removed from the abdomen.

In addition, the known trocar has been constructed so that the housing secured to the stylet can be fitted into and rotated relative to a second housing containing an outer tube through which the stylet and protective tube may pass. Further, the second housing has had a flap valve which cooperates with a groove in the protective tube in order to lock the spring-biased protective tube in an extended position over the sharp stylet tip. Generally, the trocar is delivered for use in this locked condition so as to protect the user from being injured by the sharp tip of the stylet. However, prior to use, the housing connected to the stylet must be pushed into an unlocked position so that the protective tube can retract from the sharp tip in order to puncture an abdominal wall.

In the event that the trocar is not delivered in the locked position, there is a risk that users may be damaged should the protective tube inadvertently be retracted to expose the sharp stylet tip. Further, any exposed tissue of a patient may be damaged should the protective tube be retracted inadvertently prior to proper positioning of the stylet for penetrating an abdominal wall.

Accordingly, it is an object of the invention to provide a trocar in which the risk of injury due to inadvertant retraction of a protective tube over a sharp stylet tip can be significantly reduced.

It is another object of the invention to shield the sharp tip of a stylet of a trocar in a positive manner at all times prior to actual use.

It is another object to the invention to provide a relatively simple structure for shielding the sharp tip of a trocar until ready for use.

It is another object to the invention to provide a relatively simple mechanism for unlocking a trocar for use.

SUMMARY OF THE INVENTION

Briefly, the invention provides a trocar of two part construction.

One part of the trocar is formed of a housing, a stylet which is secured to and which extends from the housing with a sharp tip at a distal end, a tube which is slidably mounted in the housing between an extended position and a retracted position with the tube disposed about the stylet and a spring in the housing for biasing the tube outwardly of the housing into the extended position. In accordance with the invention, a latch means is provided in the housing for locking the tube in the extended position and a slider is slidably mounted in and projects from the housing for releasing the latch means to permit movement of the tube into the retracted position.

The second part of the trocar comprises a second housing which is coaxial of the first housing to define a handgrip and a guide tube which is secured to and which extends from the housing with the protective tube slidably mounted therein. The housing of the second part is also provided, in known manner, with a seal ring through which the protective tube of the first part slides in seal-tight manner and a flap valve which covers over the seal ring when the first part has been removed from the second part of the trocar.

When in use, the two housings are disposed in face-to-face manner with the slider of the first housing projecting against the second housing. In this position, the protective tube is retained in a locked position by the latch means. However, when the user is ready to penetrate, for example through an abdominal wall of the patient, the two housings are squeezed together so as to push the slider into the first housing to release the latch means. At this time, the protective tube is unlatched so as to be slid proximally during penetration through an abdominal wall as is known. However, once penetration has been completed, the protective tube is spring-biased distally into the extended position and is re-engaged by the latch means so as to be locked in place. The stylet may then be removed from the abdomen while the protective tube remains in a locked protective position about the sharp tip of the stylet.

The latch means includes a leaf spring which abuts the protective tube in the extended position as well as a spring finger which extends from the leaf spring into abutment with the slider for lifting of the leaf spring from the protective tube in response to movement of the slider into the housing. In this regard, a collar is provided on the protective tube to abut the leaf spring when in the extended position. In addition, the collar is slidable along the leaf spring in order to lift and release the spring finger from the slider at an intermediate point of movement along the leaf spring. Thus, once the slider has released the latch means, and the protective tube has moved a certain distance, the slider is no longer active so that any return of the protective tube to the extended position automatically activates the latch means into the locked position preventing further proximal movement of the protective tube.

An indicator may also be secured to the protective tube for exposure through the housing of the first part to indicate the position of the protective tube relative to the stylet tip during use.

BRIEF DESCRIPTION OF THE DRAWINGS

These and other objects and advantages of the invention will become more apparent from the following description taken in conjunction with the accompanying drawings wherein:

FIG. 1 illustrates a perspective view of a trocar constructed in accordance with the invention.

FIG. 2 illustrates a cross-sectional view of the trocar of FIG. 1 in a locked position;

FIG. 3 illustrates a perspective view of a latch constructed in accordance with the invention;

DETAILED DESCRIPTION OF THE PREFERRED EMBODIMENTS

Figure 4:
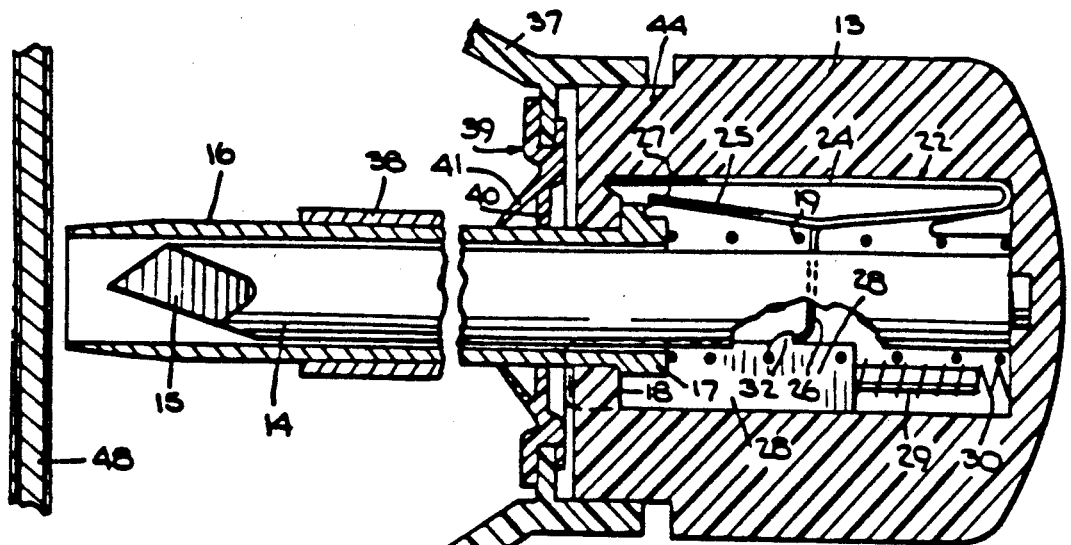
FIG. 4 illustrates a partial cross-sectional view of the trocar in a position in which the protective tube has been initially released for penetration of an abdominal wall.

Referring to FIG. 1, the trocar 10 is constructed of two parts 11, 12 which are arranged in a coaxial manner.

Referring to FIGS. 1 and 2, one part 11 includes a housing 13, for example made of plastic and a stylet 14, for example made of steel, which is secured to and extends from the housing 13 with a sharp tip 15, as is known, at the distal end. In addition, a protective tube 16, for example made of steel or aluminum is slidably mounted in the housing 13 between an extended position, as viewed in FIG. 2, and a retracted position while being disposed concentrically about the stylet 14. The tube 16 carries a collar 17 at the proximal end within the housing 13 to abut against a wall 18 of the housing under the bias of a coil spring 19. As indicated, the spring 19 is concentric to the proximal end of the stylet 14 and abuts against a back wall of the housing 13. In addition, the stylet 14 has a reduced portion 20 which is disposed within a recess 21 in the backwall of the housing 13 and secured in place, for example by an adhesive or other suitable means.

Referring to FIGS. 2 and 3, a latch means 22 is disposed in the housing 13 for locking the protective tube 16 in the extended position illustrated. As indicated in FIG. 3, the latch means 22 is in the form of a one-piece body having a flat base 24, a leaf spring 25 which extends from one end of the base 24 to define a U-shape and a spring finger 26 which extends angularly and intermediately from the leaf spring 25. As shown, the leaf spring 25 has a proximal portion of a width equal to the width of the base 24 which extends from the base 24 to an intermediate point and a distal portion of reduced width extending to the distal end. The spring finger 26 extends from this intermediate point.

Figure 7:
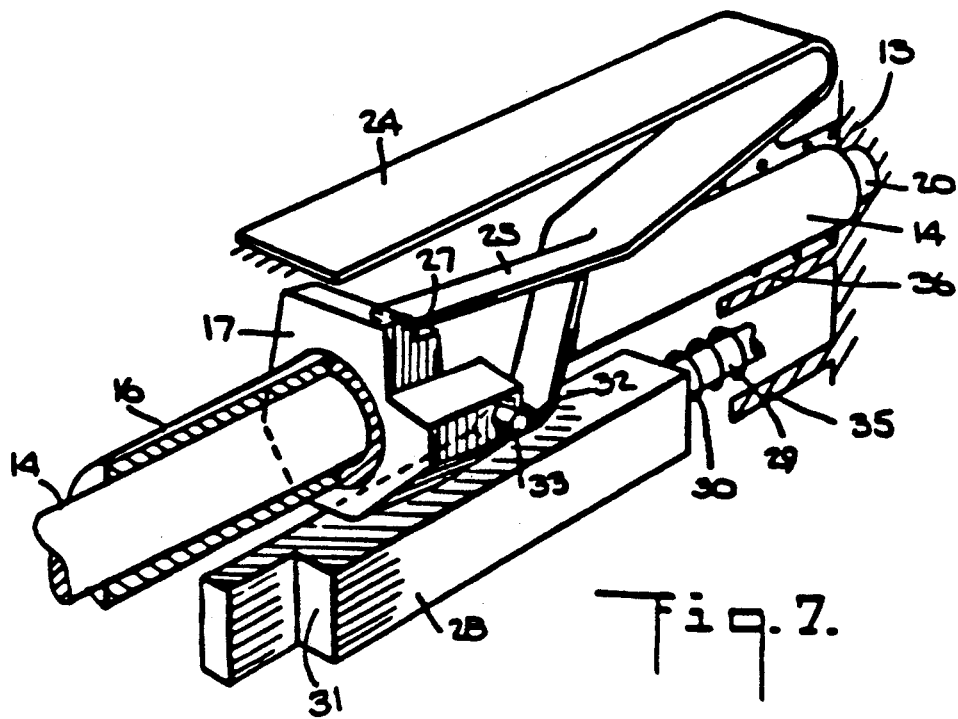
FIG. 7 illustrates a part perspective view of the latch means and slider of the trocar in a locked position.

As indicated in FIGS. 2 and 7, the reduced portion of the leaf spring 25 engages against the collar 17 on the protective tube 16. To this end, the collar 17 has a shoulder 27 at the upper end, as viewed, against which the end of the leaf spring 25 abuts. When the leaf spring 25 is in the position shown the protective sleeve 16 is prevented from moving proximally. As indicated in FIG. 2, the base 24 of the latch means is retained within the housing 13 in a fixed manner so as to be restrained against movement proximally or distally.

Referring to FIG. 2; a slider 28 is slidably mounted in and projects from the housing 13 for releasing the latch means 22 in order to permit movement of the protective tube 16 into a retracted position. The slider 28 is made of any suitable material, such as a metal or plastic and includes a stem 29 at the proximal end about which a spring 30 is disposed for biasing the slider 28 in a distal direction. As indicated, the spring 30 abuts against the back wall of the housing 13 while the slider has a shoulder portion 31 (see FIG. 7) for abutting against a front wall of the housing 13 in an extended position thereof. The slider 28 also has a shoulder 32 on an upper surface, as viewed, for engaging the free end of the spring finger 26. The shoulder 32 acts in the manner of a cam or single tooth ratchet so that when the slider 28 is moved into the housing 13 against the bias of the spring 30, the spring finger 26 pivots in a counter-clockwise manner as viewed while also lifting the leaf spring 25 from the collar 17 to release the protective tube 16 (see FIG. 4). Alternatively, other means such as a recess in the slider 28 can be used to accomplish the engagement of the spring finger 26. At this time, the tube 16 is freed to be able to move proximally, for example as indicated in FIG. 5. During this time, the collar 17 slides along the leaf spring 25 causing the leaf spring 25 to move towards the base 22 thereby lifting and releasing the spring finger 26 from the shoulder 32, for example at an intermediate point of movement of the collar 17 along the leaf spring 25.

Referring to FIG. 7, the collar 17 also carries a guide pin 33 which extends radially outwardly of the protective sleeve 16. As indicated in FIG. 1, this guide pin 33 is received in a guide slot 34 in a side wall of the housing 13. The guide pin 13 and slot 34 thus serve to retain the collar 17 in alignment with the leaf spring 25 during use. In addition, the pin 33 serves as an indicator to indicate the position of the protective tube 16 relative to the tip 15 of the stylet 14. For example, the distal most position (FIG. 1) indicates the tube 16 is in the extended position. A surgeon can thus determine where the tube 16 is during a surgical procedure.

Referring to FIG. 7, the housing 13 may be provided with a stop portion 35 for abutting the proximal end of the slider 28 and thus establish a rear most position of the slider 28. In similar manner, the housing may be provided with a stop portion 36 for abutting the collar 17 so as to provide a rear most position for the protective tube 16.

Referring to FIGS. 1 and 2, the second part 12 of the trocar 10 is constructed in conventional manner. For example, this part 12 includes a housing 37, for example of plastic and a guide tube 38 which is secured to and extends from the housing 37 so as to slidably mount the protective tube therein. In addition, a seal ring 39 is mounted within the housing 37 about an opening through which the protective tube 16 of the trocar part 11 passes. This seal ring 39 includes a main portion 40 which sealingly engages the outer peripheral of the protective tube 16 and an annular flap 41 which extends from the main portion 40 to sealingly engage the protective tube 16 at a point distal from the main portion 40. During retraction of the protective tube 16, the seal flap 41 tends to deform in an S-shape manner as indicated in FIG. 5.

The housing 37 also has a flap valve 42 pivotally mounted therein in known manner for sealing over the seal ring 39 after the trocar part 11 has been removed.

Referring to FIGS. 1 and 2, the housing 37 of the trocar part 12 is provided with a rectangular recess 43 at the proximal end while the housing 13 of the trocar part 11 is provided with a reduced portion 44 of rectangular shape which is sized to fit within the recess 43.

In addition, the housing 37 is provided with a valve construction 45 as well as a pointer 46 to indicate the position of the flap valve 42.

In order to use the trocar 10, the two housing parts 11, 12 are placed together. For example, as indicated in FIG. 2, the protective tube 16 is slid through the ring seal 40 with the flap valve resting against the outer periphery of the protective tube 16. At this time, the leaf spring 25 engages against the shoulder 27 of the collar 17 so as to lock the protective tube 16 in the extended position. Also, the slider 28 projects out of the distal face of the housing 13.

Figure 5:
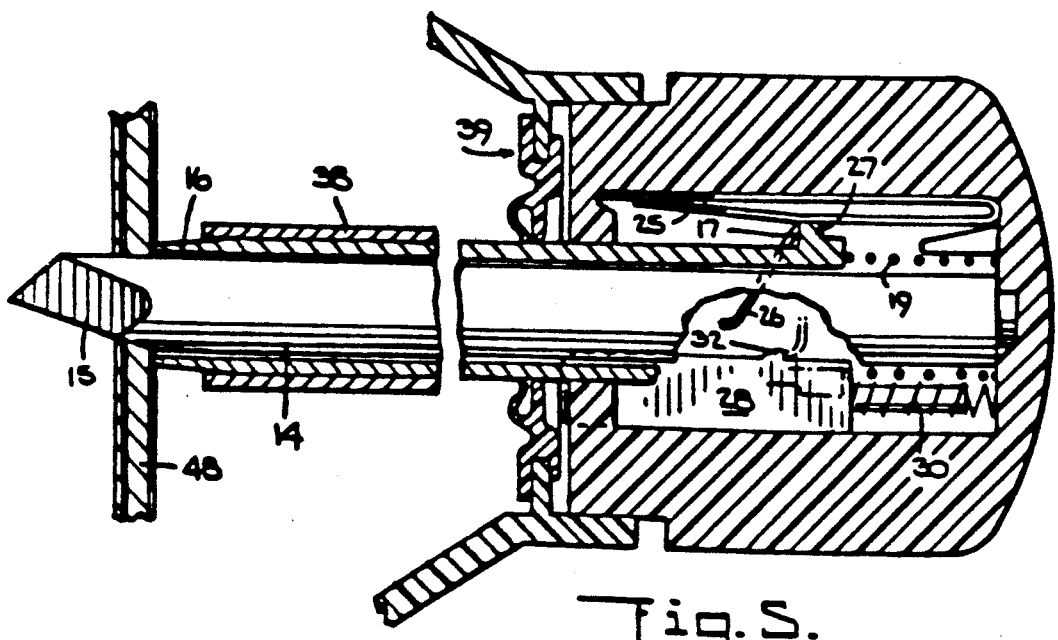
FIG. 5 illustrates a view similar to FIG. 4 with the spring finger released from the slider.

Next, as indicated in FIG. 4, the two housings 13, 37 are brought together so that the reduced portion 44 of the housing 13 moves into the recess 43 of the housing 12 with the slider 28 abutting a rear wall 47 of the housing 37. Next, the user squeezes the two housings 13, 37 together so as to move the slider 28 proximally into the housing 13. In this regard, the two housings 13, 37 function as a handgrip for the user.

As indicated in FIG. 4, when the slider has moved into the housing 13, the spring finger 26 is pivoted in a counterclockwise manner via the shoulder 32 on the slider 28 while also moving upwardly to lift the leaf spring 25 from the shoulder 27 of the collar 17. In the position shown, the protective tube 16 is free to move relative to the stylet 14. The user then penetrates through the abdominal wall 48 of a patient in known manner so that the sharp tip 15 of the stylet 14 punctures the wall 48 as indicated in FIG. 5. During this initial phase, the protective tube 16 moves proximally within the guide tube 38 with the collar 17 sliding along the leaf spring 25. At an intermediate point, for example where the finger 26 extends from the leaf spring 25, the collar deflects the leaf spring 25 upwardly causing the spring finger 26 to lift above the shoulder 32 on the slider 28. The spring finger 26 then pivots in a clockwise manner into the full line position illustrated in FIG. 5. The protective tube 16 may slide further proximally until abutting the stop 36 (see FIG. 7).

Of note, the stylet 14, protective tube 16 and guide tube 38 are sized so that the rear most retraction of the protective tube 16 places the distal end of the protective tube 16 slightly behind the sharp tip 15 of the stylet 14 but ahead of the guide tube 38. In addition, the respective diameters of the stylet 14 and tube 16, 38 are such that a slide fit relationship is presented so that both tubes 16, 38 may follow the sharp tip 15 through the wall 48 of the patient into the interior of the abdomen, as is known.

Figure 6:
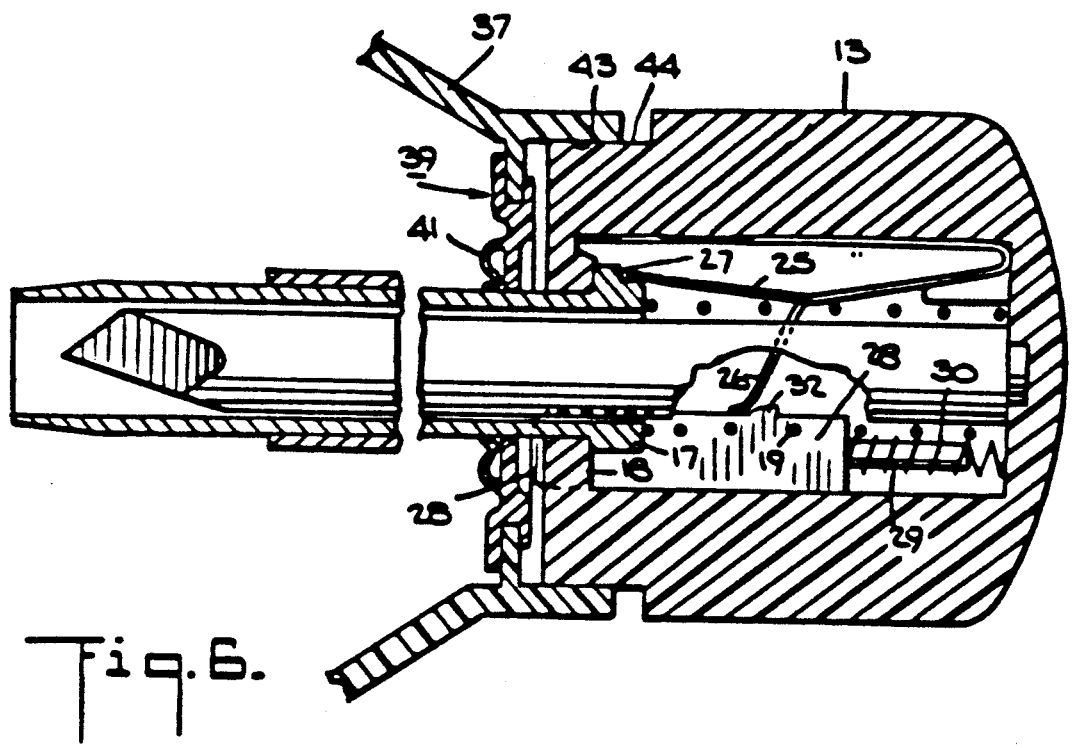
FIG. 6 illustrates a view similar to FIGS. 4 and 5 with the latch means returned to a locked position with the protective tube in an extended position.

After the protective tube 16 passes through the final layer of the abdominal wall 48 and the sharp tip 15 is within an inflated cavity between the abdominal wall 48 and other organs, which cavity has been intentionally inflated, the spring 19 pushes the protective tube 16 outwardly to the extended position indicated in FIG. 6. At this time, the leaf spring 25 re-engages the shoulder 27 of the collar 17 to lock the protective tube 16 in place over the stylet tip 15. As indicated, the spring finger 26 is on the distal side of the shoulder 32 of the slider 28 and cannot be triggered again unless returned to the position indicated in FIG. 2.

The user may then release the housings 13, 37. Next, for example, the trocar part 11 may be slid out of the trocar part 12 with the flap valve 42 closing over the ring seal 40. This component 12 may then be used in a conventional manner. The removed component 11, on the other hand, has the guide tube 16 locked in place over the stylet tip 15 so as to protect against injury from the sharp edges of the tip 16.

In the event that the trocar 10 would require a second triggering of the latch means 22, the trocar part 11 can be slid slightly out of the housing 37 so that the slider 28 again projects out of the housing 13 so that the spring finger 26 engages behind the shoulder 32. A further squeezing action can then be carried out to again release the guide tube 16 in the manner described above.

The invention thus provides a trocar which can be easily manipulated by a user while the sharp tip of the stylet is maintained in a protective environment by the protective tube.

Further, the invention provides a trocar in which the protective tube is maintained in a locked position relative to the stylet tip until actual penetration through an abdominal wall or the like is required.

Of note, instead of using a latch means wherein a base and a leaf spring define a U-shape, the latch means may simply constitute a leaf spring mounted directly to the housing in a cantilevered manner with the spring finger depending therefrom.

What is claimed is:

1. A trocar comprising:
    a first housing;
    a stylet secured to and extending from said first housing, said stylet having a sharp tip at a distal end;
    a protective tube slidably mounted in said first housing between an extended position and a retracted position, said protective tube being disposed concentrically about said stylet;
    a spring in said first housing biasing said protective tube into said extended position;
    latch means disposed in said first housing, said latch means comprising a base and a leaf spring, said base and leaf spring being joined at a hinge and said leaf spring being adapted to move between a deflected and a non-deflected position relative to said hinge, said leaf spring engaging said protective tube for releasably locking said protective tube in said extended position when said leaf spring is in said non-deflected position;
    means mounted in and projecting from said first housing for disengaging said leaf spring from said protective tube by moving said leaf spring into said deflected position in order to permit movement of said protective tube into said retracted position;
    a second housing; and
    a guide tube secured to and extending from said second housing configured and dimensioned to slidably receive said protective tube;
    wherein said leaf spring automatically returns to said non-deflected position and re-engages said protective tube when said protective tube moves from said retracted position to said extended position.

2. The trocar according to claim 1 further comprising:
    a collar disposed on said protective tube, said leaf spring engaging said collar with said protective tube in said extended position.

3. The trocar according to claim 1 wherein said collar includes a shoulder, said leaf spring abutting said shoulder with said protective tube in said extended position.

4. The trocar according to claim 1, wherein said collar completely surrounds said protective tube.

5. The trocar according to claim 4, further comprising alignment means connected to and extending from said collar for maintaining alignment between said collar and said latch means.

6. The trocar according to claim 5, wherein said alignment means further comprise a guide pin extending from said collar to engage a slot in said first housing.

7. The trocar according to claim 2, further comprising position indicating means connected to and extending from said protective tube for indicating the position of said protective tube.

8. The trocar according to claim 7, wherein said position indicating means further comprise a pin extending from said collar into a slot in said first housing.

9. The trocar according to claim 1, wherein said means for disengaging said leaf spring further comprise a slider mounted in and extending from said first housing, said slider disengaging said leaf spring from said protective tube in response to force urging said slider into said first housing.

10. The trocar according to claim 9, wherein said leaf spring further comprises a first portion engaging said protective tube and a second, finger portion extending angularly from said first portion, said second portion engaging said slider.

11. The trocar according to claim 10, wherein said slider further includes a shoulder which urges said finger portion to move said leaf spring from said non-deflected position to said deflected position and to thereby disengage said leaf spring from said protective tube as said slider is urged into said first housing.

12. The trocar according to claim 11 wherein said leaf spring assumes a first, locked position with said first leaf spring portion engaging said protective tube, a second, unlocked position with said first leaf spring portion disengaged from said protective tube so that said protective tube may move from said extended position to said retracted position, and a third position with said protective tube in said retracted position, said leaf spring in said third position being biased to resume said first leaf spring position as said protective tube resumes said extended position.

13. The trocar according to claim 12 further comprising a collar on said protective tube, said leaf spring engaging said collar when said leaf spring assumes said first position.

14. The trocar according to claim 12 wherein said slider extends from said first housing with said leaf spring in said first, locked position.

15. The trocar according to claim 1, wherein said means for disengaging said leaf spring further comprise a disengagement member mounted in and extending from said first housing, said disengagement member moving said leaf spring from said non-deflected position to said deflected position in response to force urging said disengagement member into said first housing.

16. The trocar according to claim 15, wherein said disengagement member is biased to extend from said first housing toward said second housing when said protective tube is received by said guide tube.

17. The trocar according to claim 1 wherein said leaf spring assumes a first, locked position engaging said protective tube, a second, unlocked position disengaged from said protective tube so that said protective tube may move from said extended position to said retracted position, and a third position with said protective tube in said retracted position, said leaf spring in said third position being biased to resume said first leaf spring position as said protective tube resumes said extended position.

18. The trocar according to claim 1 wherein said second housing has an opening to receive said protective tube, said second housing opening having a sealing member mounted about said opening for sealingly engaging said protective tube.

19. The trocar according to claim 18 wherein said sealing member further comprises a seal ring having a main portion which sealingly engages the outer surface of the protective tube and an annular flap which extends from said main portion to sealingly engage the protective tube at a point distal to said main portion.

20. The trocar according to claim 19 further comprising a flap valve pivotally mounted in said second housing, said flap valve being received by said seal ring to seal said housing opening in the absence of a protective tube.

21. In a trocar, the combination comprising:
 a stylet with a sharp tip and a protective tube disposed concentrically about the stylet extending from a first housing, said protective tube being spring-biased into an extended position and movable into a retracted position;
 latch means disposed in said first housing, said latch means comprising a base and a leaf spring, said base and leaf spring being joined at a hinge and said leaf spring being adapted to move between a deflected and a non-deflected position relative to said hinge, said leaf spring engaging said protective tube in said extended position to releasably lock said protective tube in said extended position;
 means disposed in said first housing for disengaging said leaf spring from said protective tube by moving said leaf spring into said deflected position in order to permit movement of said protective tube into said retracted position;
 a second housing coaxial of said first housing to define a handgrip therewith; and
 a guide tube secured to and extending from said second housing with said protective tube slidably mounted therein;
 wherein said leaf spring automatically returns to said non-deflected position and re-engages said protective tube when said protective tube moves to said extended position.

22. The trocar according to claim 21 further comprising a collar on said tube, said leaf spring abutting said collar with said tube in said extended position.

23. The trocar according to claim 22, said collar further including a shoulder configured and dimensioned to abut said leaf spring.

24. A method of using a trocar comprising the steps of:
 i) providing a trocar having:
  a first housing;
  a stylet secured to and extending from said first housing, said stylet having a sharp tip at a distal end;
  a protective tube slidably mounted in said first housing between an extended position and a retracted position, said protective tube being disposed concentrically about said stylet;

a spring in said first housing biasing said protective tube into said extended position;

latch means disposed in said first housing, said latch means comprising a base and a leaf spring, said base and leaf spring being joined at a hinge and said leaf spring being adapted to move between a deflected and a non-deflected position relative to said hinge, said leaf spring releasably engaging said protective tube to lock said protective tube in said extended position;

means disposed in said first housing for disengaging said leaf spring from said protective tube by moving said leaf spring into said deflected position in order to permit movement of said tube into said retracted position; and a second housing coaxial of said first housing having a guide tube secured to and extending from said second housing with said protective tube slidably received in said guide tube;

ii) activating said means for disengaging said leaf spring;

iii) urging said protective tube and said stylet against body tissue to be penetrated, whereby said protective tube is urged into said retracted position by the body to expose said stylet to penetrate the body tissue and said leaf spring is biased to automatically resume said non-deflected position upon return of said protective tube to said extended position.

25. The method according to claim 24, wherein said means for disengaging said leaf spring includes a disengagement member extending from said first housing, and said step of activating said means for disengaging said leaf spring further comprises:

urging said first housing toward said second housing, said second housing contacting said disengagement member and urging said disengagement member into said first housing to disengage said leaf spring from said protective tube.

* * * * *